(12) United States Patent
Lemmon et al.

(10) Patent No.: US 6,558,624 B1
(45) Date of Patent: May 6, 2003

(54) METHOD AND ANALYTICAL SYSTEM FOR RAPID SCREENING OF COMBINATORIAL LIBRARIES

(75) Inventors: John Patrick Lemmon, Delanson, NY (US); Radislav Alexandrovich Potyrailo, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/626,261

(22) Filed: Jul. 25, 2000

(51) Int. Cl.[7] .............................................. G01N 30/96
(52) U.S. Cl. ........................ 422/69; 422/55; 422/63; 422/67; 422/82.05; 422/82.09; 436/173
(58) Field of Search ............................... 422/55, 63, 67, 422/69, 81, 82.05, 82.09; 436/173

(56) References Cited

U.S. PATENT DOCUMENTS

| | | | | |
|---|---|---|---|---|
| 4,558,012 A | * | 12/1985 | Nygren et al. | 436/501 |
| 4,608,231 A | * | 8/1986 | Wittty et al. | 422/61 |
| 5,306,426 A | * | 4/1994 | Afeayn | 210/635 |
| 5,496,741 A | * | 3/1996 | Pawliszyn | 436/328 |
| 5,606,008 A | | 2/1997 | Sakashita et al. | |
| 5,776,359 A | | 7/1998 | Schultz et al. | |
| 5,840,246 A | | 11/1998 | Hammons et al. | |
| 5,846,396 A | | 12/1998 | Zanzucchi et al. | |
| 5,854,684 A | | 12/1998 | Stabile et al. | |
| 5,866,430 A | * | 2/1999 | Grow | 436/172 |
| 5,923,421 A | * | 7/1999 | Rajic et al. | 356/328 |
| 5,985,356 A | | 11/1999 | Schultz et al. | |
| 6,034,775 A | * | 3/2000 | McFaralnd et al. | 356/364 |
| 6,210,571 B1 | * | 4/2001 | Zambias et al. | 310/198.2 |

* cited by examiner

Primary Examiner—T. Tung
Assistant Examiner—Yelena Gakh
(74) Attorney, Agent, or Firm—Noreen C. Johnson; Christian G. Cabou (57) ABSTRACT

Rapid, sensitive detection of analytes in small-scale samples is achieved with an analytical method in which samples are adsorbed on a sorbent material and probed spectroscopically. The method is suitable for monitoring the progress of reactions in combinatorial screening experiments.

15 Claims, 5 Drawing Sheets

METHOD AND ANALYTICAL SYSTEM FOR RAPID SCREENING OF COMBINATORIAL LIBRARIES

BACKGROUND

1. Field of the Invention

The present invention relates to a method and analytical system for rapid detection of one or more analytes in a plurality of samples. More specifically, the invention involves rapid spectroscopic detection of one or more analytes in a plurality of samples.

2. Discussion of Related Art

Analytical measurements of multiple samples can be performed one at a time using traditional separation, spectroscopic, electrochemical, gravimetric, and other techniques. These traditional measurements can be time consuming if a large number of samples is involved. Such measurements are also too slow to enable rapid characterization of dynamic processes in a multi-sample array.

Recent spectroscopic imaging techniques can lead to increased sample throughput. With parallel spectroscopic imaging of large sample arrays, the measurement time is nearly independent of the number of samples. This advantage makes possible rapid analysis of even highly dense combinatorial arrays. U.S. Pat. No. 5,854,684 to Stabile et al. and U.S. Pat. No. 5,776,359 to Schultz et al. describe techniques for imaging sample arrays by a variety of spectroscopic techniques. However, in a large variety of applications, the difference in the optical property of each of the samples is undetectable using presently available instruments. This is particularly true for small samples.

As such, there remains a need for a method for rapid analysis of large numbers of samples with sufficient sensitivity to allow for small sample sizes.

SUMMARY OF THE INVENTION

Accordingly, an exemplary embodiment of the present invention is directed to a method for analysis of at least one analyte. The method includes the steps of providing a plurality of fluid analytical samples comprising at least one analyte; providing an analytical matrix comprising a plurality of spatially differentiated analytical sites, each having a sorbent material; and delivering a known amount of each fluid analytical sample onto at least one of the analytical sites. At least one delivered analytical sample is irradiated with a first wavelength range, and a second wavelength range is detected which corresponds to a spectroscopic response of at least one analyte. A concentration of at least one analyte is determined based on the detected spectroscopic response.

Another embodiment is directed to an analytical system comprising a plurality of analytical samples each having at least one analyte. The system also includes an analytical matrix having a plurality of spatially differentiated analytical sites, each comprising a sorbent material. A sample loader for delivering a known amount of each analytical sample onto at least one analytical site is provided along with a light source for irradiating at least one analytical site on the matrix with a first wavelength range. A detector is provided to detect a spectroscopic characteristic of the analyte from at least one analytical site on the matrix with a second wavelength range. A computer determines a concentration of the analyte at least one analytical site based on the detected spectroscopic characteristic.

BRIEF DESCRIPTION OF THE DRAWINGS

Various features, aspects, and advantages of the present invention will become more apparent with reference to the following description, appended claims, and accompanying drawings, wherein

DETAILED DESCRIPTION OF PREFERRED EMBODIMENTS

Rapid and convenient analysis of at least one analyte is provided by a method comprising: providing a plurality of fluid analytical samples comprising at least one analyte for which the concentration is to be determined; providing an analytical matrix comprising a plurality of spatially differentiated analytical sites, each site comprising a sorbent material; delivering a known amount of each fluid analytical sample onto at least one unique analytical site; irradiating at least one delivered analytical sample on at least one analytical site with a first wavelength range; detecting the response of the at least one irradiated analytical sample on at least one analytical site with a second wavelength range corresponding to a spectroscopic response of the at least one analyte; and determining a concentration of the at least one analyte in at least one analytical sample based on the detected response of the at least one irradiated analytical sample on at least one analytical site.

The exemplary method provides a plurality of fluid analytical samples comprising at least one analyte for which the concentration is to be determined. The analyte may be volatile or non-volatile. As described in greater detail below, the ability to produce a signal at a given analytical site is primarily dependent on the existence of a mutual affinity between the analyte and the sorbent material that concentrates the analyte on the surface of the sorbent material. In a preferred embodiment, the analyte is non-volatile. In this context, a non-volatile analyte is an analyte that is a liquid at 25° C. and has a boiling point greater than 150° C., or an analyte that is a solid at 25° C. and has a vapor pressure of less than 0.01 torr at 25° C.

A preferred analytical sample comprises the reaction mixture produced by the reaction between dimethyl carbonate and another reactant, which may be in liquid, solid, or gaseous state, to form a dialkyldialkoxysilane, preferably dimethyldimethoxysilane, or a tetraalkoxysilane, preferably tetramethoxysilane. The reaction mixture may comprise a catalyst. Another preferred analytical sample comprises the reaction mixture produced by the reaction between acetone and phenol to produce bisphenol A (BPA). The analytical sample may optionally comprise a solvent, which may be aqueous, organic, mixed organic, or any miscible mixture of aqueous and organic solvents. Another preferred analytical sample comprises a polycarbonate polymerization reaction mixture in which the analyte is a dihydric phenol. In addition to the dihydric phenol, the reaction mixture may additionally comprise one or more of a diaryl carbonate, a carbonyl halide (e.g., phosgene), a polycarbonate, a reaction catalyst, one or more reaction by-products (e.g., phenol), water, and one or more organic solvents (e.g., acetone, dichloromethane and acetonitrile). Art-recognized polycarbonate polymerization reactants, products, catalysts and solvents are described in, for example, U.S. Pat. No. 5,606,008 to Sakashita et al. An especially preferred dihydric phenol analyte is 2,2-bis(4-hydroxyphenyl)propane (bisphenol A; BPA; CAS Registry No. 80-05-7).

The analytical matrix comprises a plurality of spatially differentiated analytical sites, each site comprising a sorbent material. Preferably, the sorbent material is any suitable material effective for sorption of the analyte, and the selection of a sorbent material will, of course, depend on the chemical nature of the analyte. The sorbent material's sorption of the analyte effectively concentrates the analyte and enables high analytical sensitivity. Exemplary sorbent materials are well known in the art and include activated carbon, silica, alumina, diatomaceous earth, zeolite molecular sieves, carbon molecular sieves, metallic particles, semiconductor particles, dielectric particles, polymeric sorbents, and mixtures comprising at least one of the foregoing.

The polymeric sorbents may include natural rubber and polymers formed at least in part from the polymerization of dienes, polyethylenes and polypropylenes, elastomeric polyesters, alkenyl aromatic resins, silicones, silicone polyimides, polyurethanes, polyphenylene ethers, and the like. The sorbents may have particle sizes ranging from about 1 nanometer to about 1 millimeter. Chemically modified sorbents are expressly included (for example, a silica gel with a hydrophobic coating of covalently attached $C_{18}$ carbon chains). Specific sorbent materials are well known to those of ordinary skill in the art in connection with, for example, gas chromatography and liquid chromatography techniques. Illustrative sorbent materials include the poly (ethylene oxide) materials having weight average molecular weights greater than 1,000,000, available from Aldrich; the poly(2,6-diphenyl-p-phenylene ether) materials under the trademark TENAX® available through Alltech Associates, Inc.; the graphitized carbon-based adsorbents available under the trade names CARBOPACK and CARBOTRAP through Alltech Associates; the carbon molecular sieves available under the trade names CARBOXEN and CARBOSIEVE through Supelco Incorporated, Bellefonte, Pa.; the family of styrene divinyl benzene polymers, ethyl vinyl and divinyl benzene polymers, vinyl pyrrolidone polymers, and vinyl pyridine polymers available under the tradename PORAPAK through Alltech Associates, Inc.; the diatomite-based and polymer-based (styrene divinyl benzene polymers, cross-linked polystyrene, polyacrylonitrile and cross-linked acrylic esters) sorbent materials and adsorbents for chromatography available under the trademark CHROMOSORB® through Aldrich Chemicals; and the treated diatomaceous earth under the trademark GAS-CHROM® available through Alltech Associates, Inc. When the analyte is bisphenol A, preferred sorbent materials include functionalized polystyrene, specifically polystyrene functionalized with 5% by weight phenyl groups. When the analyte is dimethoxydimethylsilane, preferred sorbent materials include polystyrene resins and functionalized polystyrene resins, as well as silica gels finer than about 200 mesh. Mixtures of two or more sorbent materials may be used, and additional ingredients, such as binders and surfactants, may optionally be added to the sorbent material. Different surfactants can be used to control liquid penetration into the sorbent material. These can include anionic, cationic and nonionic surfactants.

The amount of sorbent material employed per analytical site may vary widely and need only be effective to accommodate the delivered amount of analytical sample without exceeding saturation. The amount of sorbent material will therefore vary roughly in proportion to the known amount of analytical sample. Generally, each analytical site will include about 1 microgram to about 500 milligrams of sorbent material.

The analytical matrix is prepared to provide a plurality of spatially differentiated analytical sites. For example, a portion of sorbent material may be distributed into each well of a 96-, 384-, or 1536-well plate. These plates and related plates are well known and commercially available. However, custom made plates can obviously be used as well. The exact number of analytical sites may vary widely, from two to about one million or more sites. For example, U.S. Pat. No. 5,854,684 to Stabile et al. describes analytical matrices comprising at least one million sites arranged in a density of at least about 10 sites per square centimeter, and U.S. Pat. No. 5,840,246 to Demers et al. provides details for a 7.25 square inch analytical matrix comprising 99,856 sites. In a preferred embodiment, the analytical sites are of uniform geometry and are uniformly distributed throughout all or a portion of the analytical matrix. In an alternative embodiment, the sorbent material is distributed uniformly about an area of the analytical matrix, and spatial differentiation of analytical sites is provided by delivery of analytical samples to spatially differentiated sites within the uniformly distributed sorbent material.

Delivery of a known amount of each analytical sample onto at least one unique analytical site may be accomplished by a sample loader comprising any means capable of accurately and reproducibly delivering a known amount, where the known amount is expressed in dimensions of mass or volume. Use of the term "unique analytical site" is meant to convey that only one analytical sample is transferred to a given analytical site. Suitable art-recognized delivery devices include microvolume syringes, peristaltic pumps, electrode-based micropumps (such as those described in U.S. Pat. No. 5,846,396 to Zanzucchi et al.), sprayers, and piezoelectric pumps. In a preferred embodiment, delivery is by microvolume syringe. The known amount may be the same or different for different analytical samples. Also, when the same analytical sample is delivered onto more than one analytical site, the known amount of the sample may be the same or different between the multiple sites. In a preferred embodiment, the same known amount of each analytical sample is delivered onto at least two, preferably at least three analytical sites, allowing the analyte concentration for a single analytical sample to be determined by using spectroscopic responses from multiple analytical sites. In general, the known amount of analytical sample is about 1 picoliter to about 1 milliliter. Preferred known amounts will depend on the application and on the delivery method. For example, analytical matrices with high analytical site densities may use volumes of about 1 to about 1000 picoliters, delivered, for example, by a piezoelectric pump. Analytical matrices with fewer analytical sites and lower analytical site densities may use volumes of 1 to 100 microliters, delivered, for example, by a multichannel syringe pump.

While the method has been described in terms of adding a single analytical solution to each analytical site, it is expressly contemplated to combine more than one solution prior to analysis. For example, by adding two or more reagent solutions to each analytical site, the site can function as a reaction cell. In this case, the solutions may be combined and the reaction conducted prior to the addition of the sorbent material and solvatochromic dye.

Once the analytical samples have been delivered onto the analytical matrix, the matrix may optionally be subjected to conditions effective to substantially evaporate at least one component of at least one of the analytical samples. Substantial evaporation of a component is defined as reduction of the original concentration of the component by at least 80%. It is preferred to reduce the concentration by at least 90%, and more preferred to reduce the concentration by at least 95%. The evaporative conditions will vary depending on the component to be removed, from leaving the matrix at ambient temperature and pressure for a few minutes, for example, to the use of one or more of elevated temperatures, reduced pressures, atmosphere exchange, infrared radiation, microwave radiation, extended times, and the like. The evaporation conditions are adjusted to avoid driving off (e.g., evaporating or subliming) or chemically reacting the analyte or the sorbent material. Where the analyte is bisphenol A, the evaporative conditions are preferably effective to substantially evaporate at least one of acetone, acetonitrile, phenol and water, without significantly affecting the concentration of bisphenol A. Where the analyte is dimethoxydimethylsilane, the evaporative conditions are preferably effective to substantially evaporate dimethyl carbonate. Typically, these conditions are quite mild, involving ambient temperature and ambient or slightly reduced pressures (i.e., pressures of 1 to 760 torr).

Spectroscopic determination of the analyte may utilize any suitable spectroscopic technique. Included among these are ultraviolet-visible absorption, infrared absorption, Raman spectroscopy, luminescence and fluorescence. A presently preferred spectroscopic technique is Raman spectroscopy. Spectroscopic determination of the analyte concentration at an analytical site involves illumination of the delivered analytical sample at that site with a first selected wavelength range $\lambda_1 - \lambda_2$ and detection at a second selected wavelength range $\lambda_3 - \lambda_4$ which is bathochromically displaced from $\lambda_1 - \lambda_2$. It will be understood that some spectroscopic techniques, such as infrared and Raman spectroscopies, customarily express wavelengths as wavenumbers ($cm^{-1}$), and that the two are interconvertible. The bandwidths defined by $\lambda_1 - \lambda_2$ and $\lambda_3 - \lambda_4$ can independently be as narrow as a fraction of a nanometer or as wide as several tens of nanometers. The choice of wavelength values $\lambda_1, \lambda_2, \lambda_3$ and $\lambda_4$ will depend on the spectroscopic technique, the analyte and the sensitivity of the detector. For Raman spectroscopy, a bandwidth less than about 1 $cm^{-1}$ is typically used for irradiation, and a bandwidth of about 1 to about 4000 $cm^{-1}$ is typically used for detection. The selection of irradiation and detection wavelengths will also depend on the analyte and sorbent material. For example, as described in detail below, sensitive detection of the analyte bisphenol A using the sorbent material functionalized polystyrene was achieved using irradiation at 785 nm.

While it may be desirable to illuminate substantially all analytical sites simultaneously at time t and detect substantially all sites simultaneously at time t+Δt, where Δt represents the time required for light to travel from the light source to the detector, some illumination devices (e.g., lasers) may prefer illumination of an individual site or a small number of sites at a given time. In such cases, it is, of course, possible to employ multiple light sources to speed data acquisition. Light sources suitable for Raman spectroscopy include lasers with various wavelengths, with 785 nm being one suitable wavelength. Other light sources include tungsten or deuterium lamps.

Detection can be accomplished with any suitable array detection device. Examples include charge-coupled devices (CCD), charge-injection devices (CID), complementary metal oxide semiconductor (CMOS) devices, photodiode arrays, and photodetector arrays, all of which are commercially available. The array detection device preferably has sufficient resolution that each analytical site is uniquely imaged by at least one, preferably at least nine, more preferably at least 25 pixels. Raw data corresponding to detection of each analytical site maybe stored temporarily in the detection device or immediately transferred to a computer. A presently preferred detector is a cooled CCD detector with detection wavelength variable according to the vibrational frequency of the analyte of interest. For detection of bisphenol A and dimethyldimethoxysilane, a detection wavelength range of 400 to 1500 $cm^{-1}$ is preferred, and specific preferred wavelength ranges corresponding to Raman transitions of these analytes will depend on the support employed.

Spectroscopic characterization of the analytical matrix is conducted at least after delivery of the analytical samples to the analytical matrix. For comparison purposes it may also be conducted before delivery of the analytical samples to the analytical matrix. When one or more components of the analytical matrix are intentionally volatilized after addition of analytical sample to the analytical matrix, spectroscopic characterization may be conducted both before and after volatilization of sample components. This method can be used when information about both volatile and non-volatile components is needed. Increased sensitivity may be achieved by extending times of continuous irradiation and detection, or by integrating results from multiple, temporally separated periods of irradiation and detection.

Once spectroscopic characterization of the analytical matrix is complete, raw data corresponding to detection of each site may be transferred to or recalled from the computer and converted to the corresponding analyte concentrations. This conversion may be accomplished by a previously established look-up table or conversion function derived from calibration testing. In the case of an analytical sample being tested on more than one analytical site, results for each site may be averaged or otherwise combined to generate an aggregate value and associated uncertainty using common statistical techniques.

The method may be employed to determine a suitable sorbent material for use in determination of a given analyte. In particular, the plurality of analytical sites can be used to survey the analyte sensitivity of a series of sorbent materials chosen to span values of one or more relevant parameters. These parameters can include particle size, porosity, surface area, surface energy, polarity, acidity, wettability, nucleophilicity, electrophilicity, conductivity, molecular weight (for polymeric materials), nature of any counterions, and the like. Leaving aside ancillary considerations such as cost and availability, the optimum sorbent material will be the one that strongly binds to the analyte and enhances the analyte's observed spectroscopic response. In this embodiment, the plurality of analytical samples may consist of identical samples containing a known concentration of the analyte. Alternatively, the plurality of analytical samples may comprise samples with varying known concentrations of the analyte.

Figure 1:
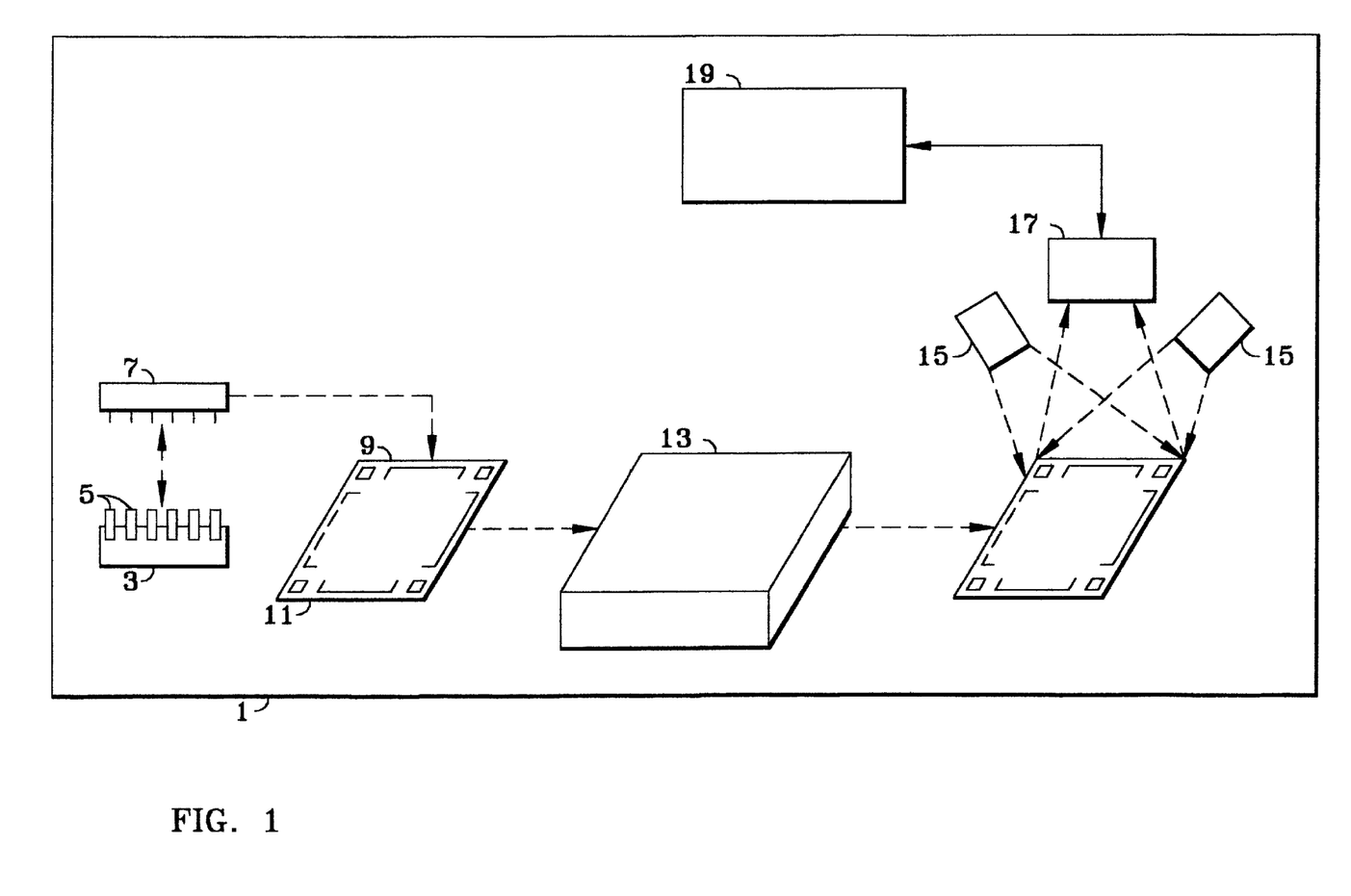
FIG. 1 is a block diagram of an aspect of an embodiment of the present invention.

FIG. 1 illustrates an exemplary analytical system 1 for carrying out the method. A plurality 3 of individual analytical samples 5 is provided. A sample loader 7 withdraws a portion of each analytical sample 5 and delivers a known amount of each sample to at least one unique analytical site 9 on an analytical matrix 11. Each analytical site comprises a sorbent material. Once the analytical samples have been delivered to the analytical matrix, the matrix is optionally transferred to an evaporator 13, where one or more volatile components of the analytical samples are evaporated. The analytical matrix is then transferred to a station where spectroscopic measurements are performed. Delivered analytical samples on the matrix are illuminated by one or more light sources 15, and the spectroscopic emissions from the irradiated samples are detected by detector 17. The detector is connected to a computer 19 to which it transfers raw spectroscopic data. Based on the raw spectroscopic data and a calibration curve or look-up table determined earlier, computer 19 calculates an analyte concentration for each analytical site on the matrix. The computer may optionally responsively control one or more of sample loader 7, evaporator 13, light source 15, and detector 17.

Figure 2:
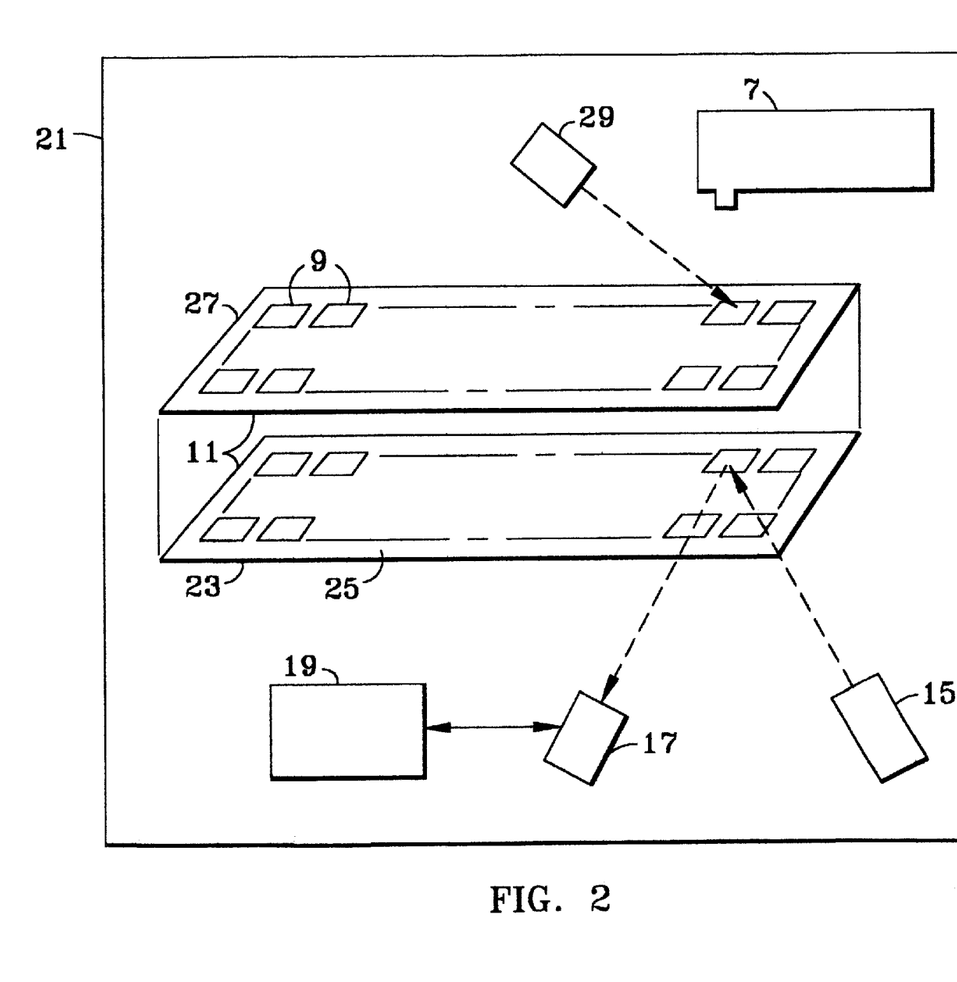
FIG. 2 is a schematic view of an aspect of an embodiment of the present invention.

FIG. 2 illustrates another embodiment of the analytical system, a small-scale reactor 21 for the rapid determination of analytes produced or consumed in small-scale reaction cells. The reactor includes a two-layer analytical matrix 11 (layers are in planar contact but shown in exploded view) consisting of a quartz substrate 23 with a thin coating of sorbent material 25 that allows for the selective preconcentration of the analyte. Reaction substrate 27 is made of a porous material, such as porous quartz, that allows for the flow of gases or liquids produced during the reactions at individual analytical sites 9 that are impregnated or overcoated with a catalyst material. Reactants are introduced to the matrix with sample loader 7 which can deliver one or more reactants. Depending on the sorbent material type, the entire analytical matrix can be heated, or one or more analytical sites can be heated by spot heater 29, which can be, for example, an infrared laser. Delivered analytical samples on the analytical sites are illuminated with light source 15, and the spectroscopic emission from the matrix is detected by detector 17. The detector is connected to a computer 19 to which it transfers raw spectroscopic data. Based on the raw spectroscopic data and a calibration curve or look-up table determined earlier, computer 19 calculates an analyte concentration for each analytical sample. The computer may optionally responsively control one or more of sample loader 7, spot heater 29, light source 15, and detector 17.

The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLE 1

This experiment demonstrates the detection of dimethoxydimethylsilane ($(Me)_2(MeO)_2Si$; CAS Registry Number 1112-39-6) on a derivatized resin sorbent material. The sorbent material was Porapak QS, obtained from Supelco. Porapak QS is a polystyrene functionalized with 5% by weight phenyl groups and having a surface area of 500–600 $m^2/g$. Approximately 100–150 milligrams of Porapak QS sorbent material was placed in a small quartz tube. One drop (approximately 1–2 microliters) of neat dimethoxydimethylsilane was placed on the sorbent material, which was then exposed to vacuum (approximately 1–5 torr) for one hour. Measurements were performed using a fiber-optic Raman system that consisted of a spectrograph, a laser, and a fiber-optic probe. The Raman spectrograph (EIC Raman Systems, model Echelle-NIR775) covered a spectral range from 200 to 3500 $cm^{-1}$ with a 4 $cm^{-1}$ resolution. This capability was available by using a gold-coated echelle grating (52.65 lines/mm) that dispersed light in two dimensions to fully exploit the CCD detector area. The detector was a Photometrics CH270 cryogenically cooled CCD camera.

Figure 3:
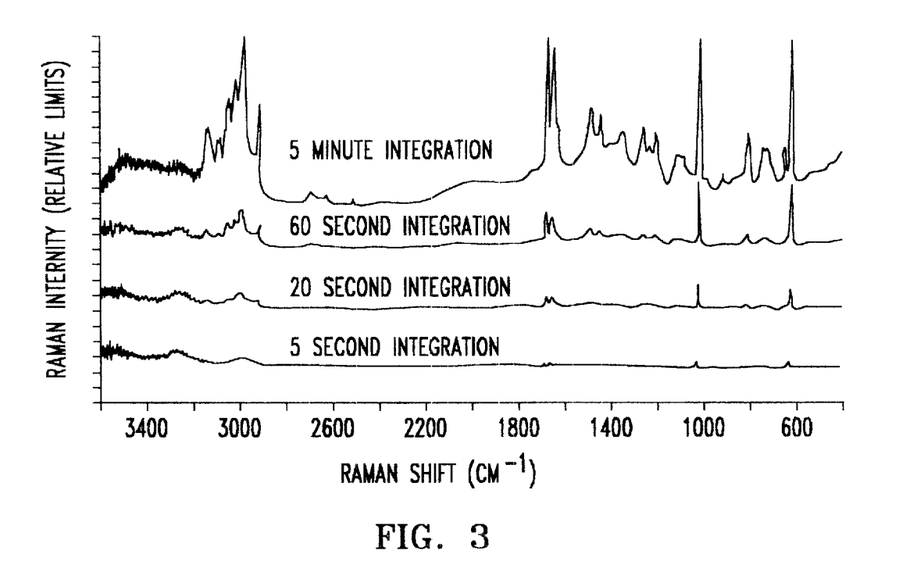
FIG. 3 shows Raman spectra corresponding to different integration times for dimethoxydimethylsilane on silica gel 425 mesh sorbent material—the excitation wavelength was 785 nm.

The light source was a wavelength stabilized high power diode laser (300 mW output power, 785 nm emission wavelength) from SDL, Inc., model SDL-8530. FIG. 3 shows the Raman spectrum of the analyte on the resin sorbent material as a function of integration time. The signal-to-noise ratio was calculated to approximately be 100 for the 5 second integration time. It should be noted that comparison experiments without sorbent material could not be conducted because the small sample volumes would evaporate or disperse. Thus, the use of a sorbent material can be a significant factor in concentrating and detecting analytes in small sample volumes.

EXAMPLE 2

This experiment demonstrates use of the method to screen sorbent materials for the analysis of dimethoxydimethylsilane. A collection of inorganic and organic sorbent materials, forming a small-scale library, was created as a function of polarity and acidity. Eight sorbent materials, each present at about 100–200 milligrams, were arranged in a 96 well microtiter plate. Dowex $H^+(SO_3)$, comprising spheres of sulfonated polystyrene crosslinked with divinylbenzene, was obtained from Dow Chemical; polypropylene oxide, weight average molecular weight 250,000, was obtained from Aldrich; neutral alumina, 80–200 mesh, was obtained from Fisher; Gas Chrom C, a silica, was obtained from Supelco; Ultem $NH^{2+}$, a polyetherimide functionalized with amine groups, was obtained from General Electric; particulate LEXAN® 140 grade polycarbonate resin 140 was obtained from General Electric; neutral alumina, 15 micrometer particle size, and acidified alumina (Alumina H+), 80–200 mesh, were obtained from Fisher; silica gel, 200 and 245 mesh, were obtained from Fisher; Amberlite COOH, cation exchange resin comprising carboxylated spheres of polystyrene spheres crosslinked with divinyl benzene, was obtained from Dow Chemical; AG3-XA4 Cl⁻, an anion exchange resin, was obtained from Dow Chemical; titanium dioxide, particle size approximately 250–500 micrometers, was obtained from Aldrich; polyethylene oxide, weight average molecular weight $5 \times 10^6$, was obtained from Aldrich; Porapak QS 80/100, a porous polymer with particle size 80/100 mesh, was obtained from Supelco; europium dioxide ($EuO_2$), particle size approximately 250–500 micrometers, was obtained from Alfa Aesar.

Figure 4:
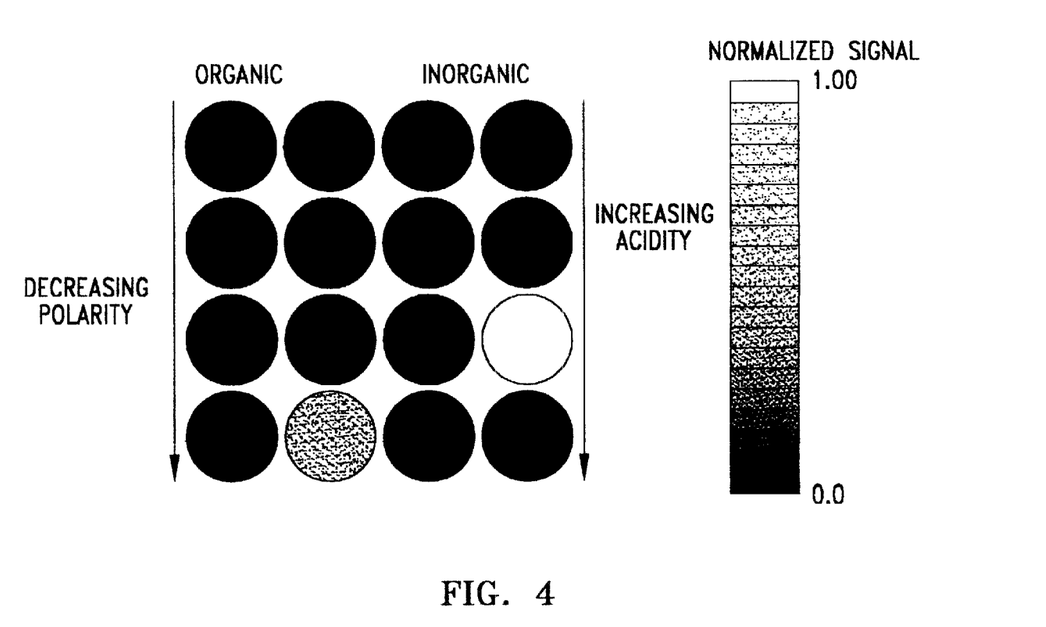
FIG. 4 is a false-colored image of a 4×4 matrix of sorbent materials with dimethoxydimethylsilane; the shades of gray, according to the scale at right, indicate the intensity of the 616 $cm^{-1}$ Si—O Raman transition of dimethoxydimethylsilane—the excitation wavelength was 785 nm.

A map of the sorbent materials, corresponding to their positions on the analytical matrix in FIG. 4, is given in Table 1.

TABLE 1

| | | | |
|---|---|---|---|
| 400 mesh Dowex H+ (SO3)-, Dow | Polypropylene oxide, Aldrich | Alumina, (neutral) 80–200 mesh, Fisher | Gas Chrom Q, Silica, Supelco |
| ULTEM NH2+, GE | Polycarbonate Resin 140 grade, GE | Alumina, (neutral) 15 μm mesh, Fisher | Silica Gel 200 Mesh, Fisher |
| Amberlite COOH Dow | AG3-XA4 Cl- Anion exchange Resin, Dow | Titanium dioxide, Aldrich | Silica Gel 425 Mesh, Fisher |
| Polyethylene oxide, Mw 5e6 Aldrich | Porapak QS80/ 100, Supelco | EuO$_2$, AlfaAesar | Alumina, H+ 80–200 Mesh, Fisher |

Figure 5:
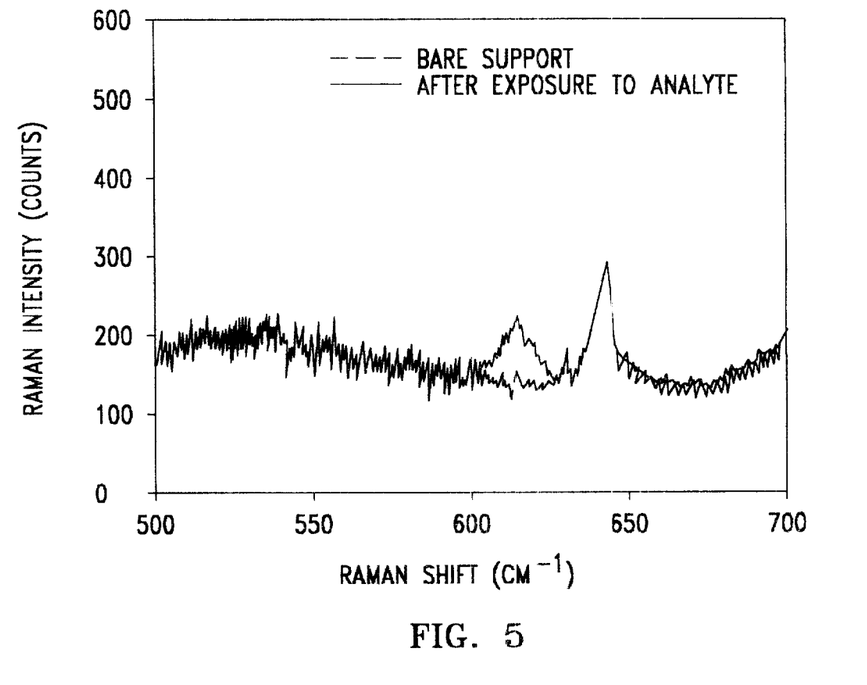
FIG. 5 shows Raman spectra of the sorbent material with and without chemically adsorbed dimethoxydimethylsilane—the peak at 616 $cm^{-1}$ can be ascribed to the analyte—the excitation wavelength was 785 nm.

A small drop (approximately 1–2 microliters) of neat dimethoxydimethylsilane was placed on each sorbent material. The sorbent materials were then dried under vacuum (approximately 1–5 torr) for one hour at ambient temperature. Raman spectra of each sorbent material were collected before and after exposure to the silane analyte using the apparatus and conditions described in Example 1. Detection utilized a 4 cm$^{-1}$ bandwidth centered at 616 cm$^{-1}$. The difference, as a function of sorbent material, in the dimethoxydimethylsilane Raman intensities before and after sample addition and vacuum drying is presented in Table 2 and FIG. 4. FIG. 4 depicts the intensity differences as a false-color image of the analytical matrix in which the scale at right relates the colors to normalized intensity differences. Intensity differences were proportional to the amount of dimethoxydimethylsilane absorbed. Two of the investigated materials, Porapak QS and Silica Gel 425 mesh, demonstrated a substantial affinity for the analyte as indicated by the intensities of their signals in FIG. 4. The best sorbent material was Silica Gel 425 mesh. Its Raman spectra, before and after exposure to analyte, are shown in FIG. 5.

TABLE 2

| sorbent material | normalized intensity difference at 616 cm$^{-1}$ (arbitrary units) |
|---|---|
| 400 mesh Dowex H+(SO3)-, Dow | 0 |
| Polypropylene oxide, Aldrich | 0 |
| Alumina, (neutral) 80–200 mesh, Fisher | 0 |
| Gas Chrom Q, Silica, Supelco | 0 |
| ULTEM NH2+, GE | 0 |
| Polycarbonate Resin 140 grade, GE | 0 |
| Alumina, (neutral) 15 μm mesh, Fisher | 0 |
| Silica Gel 200 Mesh, Fisher | 0 |
| Amberlite COOH, Dow | 0 |
| AG3-XA4 Cl-, Anion exchange Resin, Dow | 0 |
| Titanium dioxide, Aldrich | 0 |
| Silica Gel, 425 Mesh, Fisher | 2.50 |
| Polyethylene oxide, Mw 5e6, Aldrich | 0 |
| Porapak QS80/100, Supelco | 1.62 |
| EuO$_2$, AlfaAesar | 0 |
| Alumina, H+, 80–200 Mesh, Fisher | 0 |

EXAMPLE 3

The method's versatility was further demonstrated by the screening of several sorbent materials for the adsorption of bisphenol A (2,2-bis(4-hydroxyphenyl)propane; "BPA"; CAS Registry No. 80-05-07). Bisphenol A was obtained from General Electric. A 4×4 matrix of organic sorbent materials spanning a range of polarities was constructed as shown in Table 3 (matrix positions were assigned randomly). Chromosorb 3% OV-275, a porous polymer resin derivatized with dicyanoallyl, was obtained from Supelco; Porapak Q, a porous divinylbenzene-ethylstyrene copolymer resin for separating aliphatics by gas chromatography, was obtained from Supelco; C18 Porasil, a silica functionalized with C$_{18}$ groups, was obtained from Supelco; 3% Poly S, a porous polymer support, was obtained from Alltech; Chromosorb 3% OV-17, a porous phenyl methyl polymer resin, was obtained from Supelco; 3% SP2300, a poly(cyanopropylphenyl siloxane) resin, was obtained from Supelco; 3% BPHPT (bis phenyl toluidine), a derivatized porous polymer resin, was obtained from Alltech; 3% EGSS-X (ethylene succinate methyl silicone), a porous polymer resin, was obtained from Supelco; silica gel derivatized with amine (—NH$_2$) groups was obtained from General Electric; 3% Poly MPE, a porous polymer resin, was obtained from Supelco; Poly A 103, a porous polymer resin, was obtained from Alltech; 3% SP-2340, a porous polymer resin, was obtained from Supelco; Carbowax 20M, a silicone based gum, was obtained from Alltech; 6% Pentasil 350, a porous polymer resin, was obtained from Supelco; Se-52 (5% Phenyl), a phenyl-derivatized silica gel, was obtained from Supelco.

TABLE 3

| | | | |
|---|---|---|---|
| Chromosorb 3% OV-275, Supelco | Porapak Q, Supelco | C18, Porasil, C Supelco | 3% Poly S, Supelco |
| Chromosorb 3% OV-17, Supelco | 3%, Silica-10C Cyanopropyl Silicone | 3% BPHPT, Supelco | 3% EGSS-X, Supelco |
| Porapak QS, Supelco | Silica Gel w/NH2 General Electric | 3% Poly MPE, Supelco | Poly A 103, Supelco |
| 3% SP-2340, Supelco | Carbowax 20M, Supelco | 6% Pentasil 350, Supelco | Se-52 (5% Phenyl), Supelco |

Figure 6:
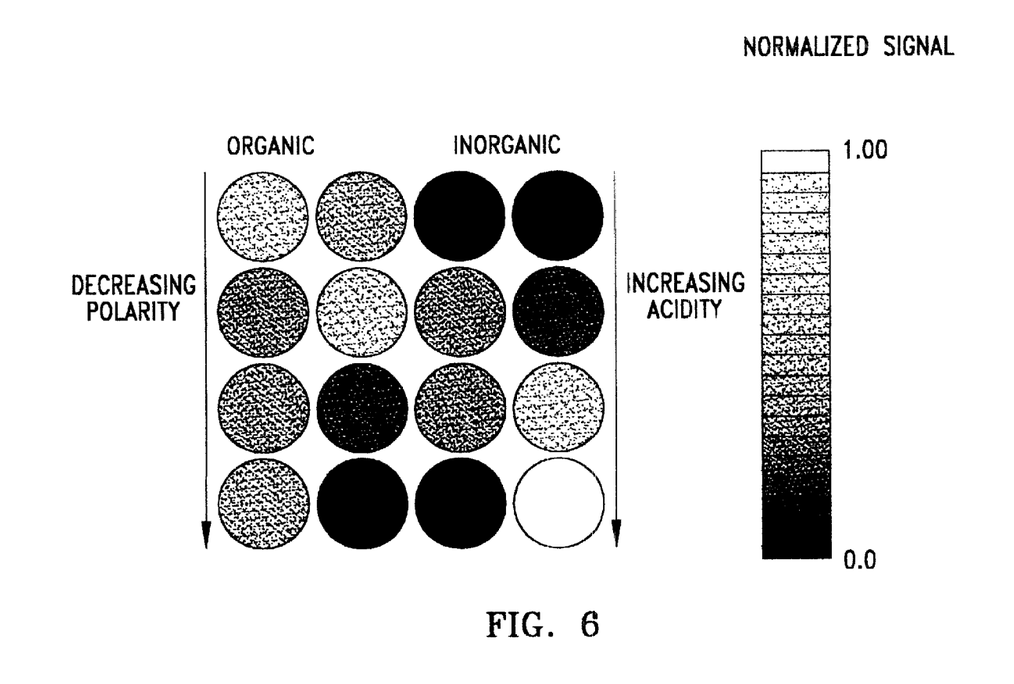
FIG. 6 is a false-colored image of a 4×4 matrix of sorbent materials with bisphenol A—the shades of gray, according to the scale at right, indicate the intensity of the 825 $cm^{-1}$ Raman transition of bisphenol A—the excitation wavelength was 785 nm.
Figure 7A:
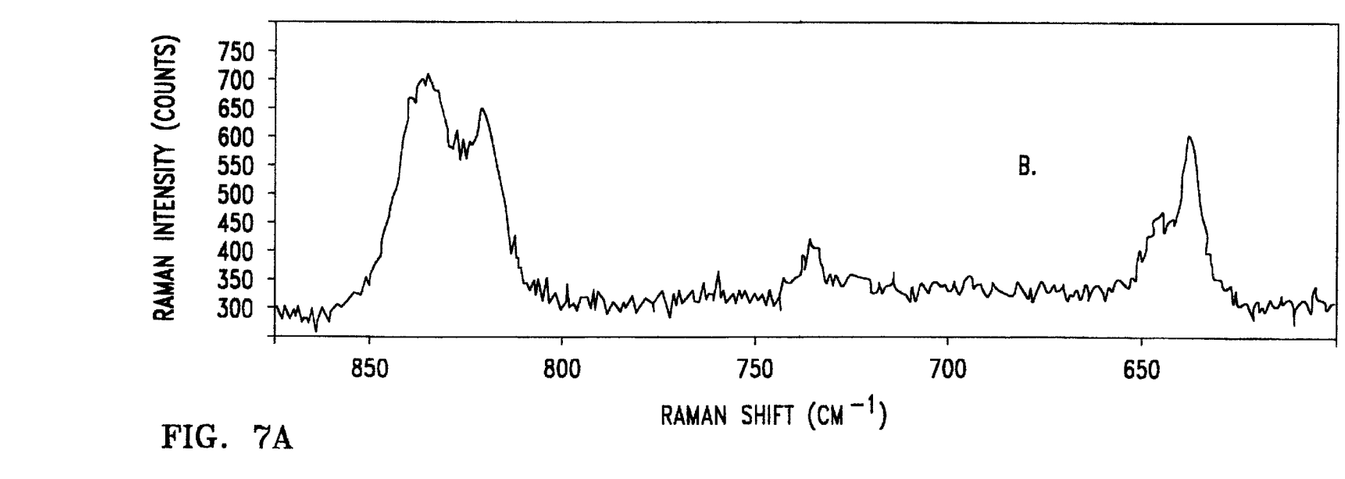
FIG. 7 shows Raman spectra of a derivatized polystyrene resin sorbent material without (A) and with (B) chemically adsorbed bisphenol A—the excitation wavelength was 785 nm and the integration time was 5 seconds.
Figure 7B:
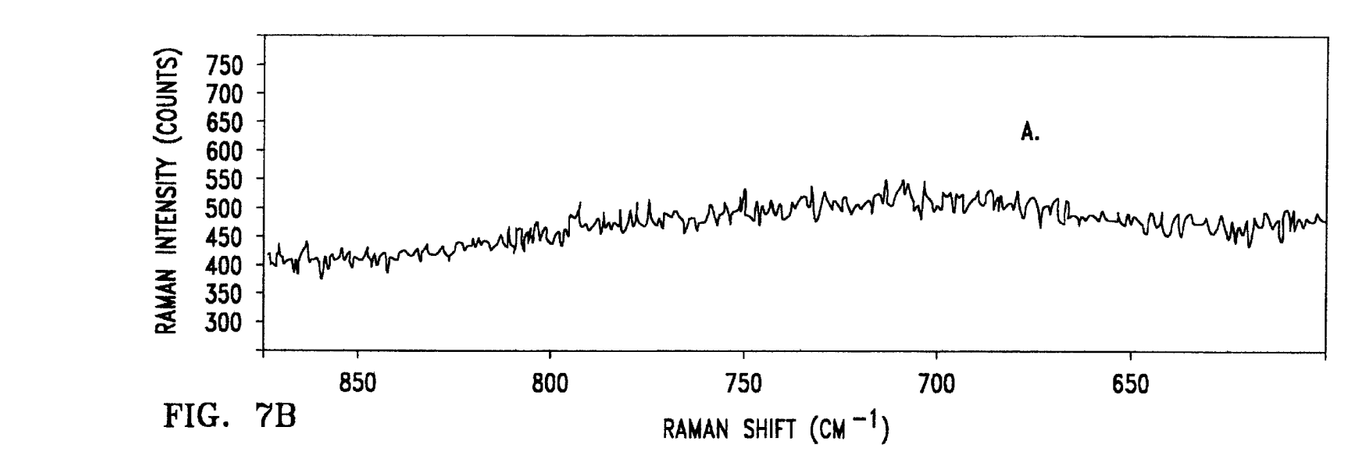

A small drop (1–2 microliters) of bisphenol A dissolved in acetone was added to each analytical site. The analytical matrix was exposed to vacuum (approximately 1–5 torr) for one hour to remove acetone. Raman spectra of each sorbent material were collected before and after exposure to the BPA analyte using the apparatus and conditions described in Example 1. The difference in intensities at 825 cm$^{-1}$ (4 cm$^{-1}$ bandwidth) before and after sample addition and vacuum drying, is given in Table 4 and presented in FIG. 6 as a false-colored image of the analytical matrix. Several sorbent materials exhibit significant affinity for bisphenol A: Chromosorb 3% OV-275, Porapak Q, Chromosorb 3% OV-17, 3% silica-10C cyanopropyl silicone, 3% BPHPT, 3% EGSS-X, Porapak QS, silica gel w/NH2, 3% poly MPE, Poly A 103, 3% SP-2340, and Se-52 (5% Phenyl). The Raman spectra of the sorbent material with the greatest BPA affinity, Porapak Q, before (A) and after (B) exposure to bisphenol A are presented in FIG. 7.

TABLE 4

| sorbent material | normalized intensity difference at 825 cm$^{-1}$ (arbitrary units) |
|---|---|
| Chromosorb 3% OV-275, Supelco | 0.738 |
| Porapak Q, Supelco | 0.521 |
| C18, Porasil, C, Supelco | 0 |
| 3% Poly S, Supelco | 0 |
| Chromosorb 3% OV-17, Supelco | 0.514 |
| 3%, Silica-10C Cyanopropyl Silicone | 0.721 |
| 3% BPHPT, Supelco | 0.441 |
| 3% EGSS-X, Supelco | 0.302 |

TABLE 4-continued

| sorbent material | normalized intensity difference at 825 cm$^{-1}$ (arbitrary units) |
|---|---|
| Porapak QS, Supelco | 0.534 |
| Silica Gel w/NH2, GE | 0.312 |
| 3% Poly MPE, Supelco | 0.461 |
| Poly A 103, Supelco | 0.761 |
| 3% SP-2340, Supelco | 0.651 |
| Carbowax 20M, Supelco | 0 |
| 6% Pentasil 350, Supelco | 0 |
| Se-52 (5% Phenyl), Supelco | 1.0 |

It will be understood that each of the elements described above, or two or more together, may also find utility in applications differing from the types described herein. While the invention has been illustrated and described as embodied in a method and analytical system for rapid screening of combinatorial libraries, it is not intended to be limited to the details shown, since various modifications and substitutions can be made without departing in any way from the spirit of the present invention. For example, custom software may be used to operate the system and various other types of screening methods may be used in conjunction with the present method. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. An analytical system for high-throughput analysis of polycarbonate synthesis, comprising:
    a plurality of analytical samples each comprising at least one analyte, wherein said analyte comprises at least one reagent, intermediate, or product of a polycarbonate synthesis reaction;
    an analytical matrix comprising a plurality of spatially differentiated analytical sites, each site comprising at least one sorbent material, wherein said sorbent is selected from the group consisting of activated carbon, silica, alumina, diatomaceous earth, zeolite molecular sieves, carbon molecular sieves, graphitized carbon-based adsorbents, metallic particles, semiconductor particles, dielectric particles, polymeric sorbents, and mixtures thereof;
    a sample loader capable of handling a plurality of samples for delivering a known amount of each analytical sample onto at least one analytical site;
    a light source for irradiating the at least one analytical site on the matrix with a first wavelength range;
    a detector for detecting a Raman spectroscopic characteristic of the analyte directly from the at least one analytical site on the matrix with a second wavelength range, wherein said Raman spectroscopic characteristic is specific to the analyte and not the sorbent; and
    a computer for determining a concentration of the analyte at the at least one analytical site based on the spectroscopic characteristic.

2. The system of claim 1, wherein the computer is placed in communication with at least one item selected from the group consisting of the sample loader, the light source, and the detector such that the computer responsively controls said at least one item.

3. The system of claim 1, further comprising a heater in thermal communication with the at least one analytical site.

4. The system of claim 1, further comprising an evaporator in communication with the analytical matrix to subject the at least one analytical site to conditions of elevated temperature, reduced pressure, or both.

5. The system of claim 1, wherein said polymeric sorbent comprises a natural rubber or polymers formed at least in part from the polymerization of dienes, polyethylenes, polypropylenes, elastomeric polyesters, alkenyl aromatic resins, silicones, silicone polyimides, polyurethanes, and/or polyphenylene ethers.

6. The system of claim 1, wherein said sorbent comprises material selected from the group consisting of: a poly (ethylene oxide) having a weight average molecular weight greater than 1,000,000; a poly(2,6-diphenyl-p-phenylene ether); a styrene divinyl benzene polymer; an ethyl vinyl benzene polymer; a divinyl benzene polymer; a vinyl pyrrolidone polymer; a vinyl pyridine polymer; a cross-linked polystryene polymer; a polyacrylonitrile polymer; a cross-linked acrylic ester, or a diatomite-based sorbent.

7. The system of claim 1, wherein the sorbent comprises a polystyrene resin, a functionalized polystyrene resin, or a silica gel, wherein said silica gel comprises a mesh of greater than 200.

8. The system of claim 1, wherein the sorbent comprises at least one material selected from the group consisting of a porous polymer resin derived with dicyanoallyl, a porous divinylbenzene-ethylstyrene copolymer resin, a porous phenyl methyl derivatized polymer resin, a porous poly (cyanopropylphenyl siloxane) resin, a porous bis phenyl toluidine derivatized polymer resin, a porous ethylene succinate methyl silicone polymer resin, a porous phenyl-derivatized polystyrene resin, a silica gel derivatized with amine groups, and a phenyl-derivatized silica gel.

9. The system of claim 1, wherein the sorbents comprise particles that range in size from 1 nanometer to 1 millimeter.

10. The system of claim 1, wherein said analyte comprises a dialkyldialoxysilane or a tetralkoxysilane.

11. The system of claim 10, wherein said analyte comprises dimethyldimethoxysilane or tetramethoxysilane.

12. The system of claim 1, wherein said analyte comprises a bisphenol.

13. The system of claim 1, wherein said analyte comprises polycarbonate.

14. The system of claim 1, wherein said matrix comprises a catalyst of the polycarbonate synthesis reaction.

15. The system of claim 1, wherein said analyte comprises a volume ranging from 1 ml to 1 picoliter.

* * * * *